(12) United States Patent
Chang et al.

(10) Patent No.: US 10,429,314 B2
(45) Date of Patent: Oct. 1, 2019

(54) EUV VESSEL INSPECTION METHOD AND RELATED SYSTEM

(71) Applicant: Taiwan Semiconductor Manufacturing Co., Ltd., Hsinchu (TW)

(72) Inventors: Chun-Lin Louis Chang, Hsinchu County (TW); Shang-Chieh Chien, New Taipei (TW); Shang-Ying Wu, Hsinchu County (TW); Li-Kai Cheng, New Taipei (TW); Tzung-Chi Fu, Miaoli County (TW); Bo-Tsun Liu, Taipei (TW); Li-Jui Chen, Hsinchu (TW); Po-Chung Cheng, Chiayi County (TW); Anthony Yen, Hsinchu (TW); Chia-Chen Chen, Hsinchu (TW)

(73) Assignee: Taiwan Semiconductor Manufacturing Co., Ltd., Hsin-Chu (TW)

(*) Notice: Subject to any disclaimer, the term of this patent is extended or adjusted under 35 U.S.C. 154(b) by 0 days.

(21) Appl. No.: 15/883,971

(22) Filed: Jan. 30, 2018

(65) Prior Publication Data
US 2019/0033225 A1 Jan. 31, 2019

Related U.S. Application Data

(60) Provisional application No. 62/539,273, filed on Jul. 31, 2017.

(51) Int. Cl.
*G01N 21/94* (2006.01)
*G01N 21/88* (2006.01)
(Continued)

(52) U.S. Cl.
CPC ........ *G01N 21/8806* (2013.01); *G01N 21/94* (2013.01); *G01N 21/95623* (2013.01);
(Continued)

(58) Field of Classification Search
CPC ............ G03F 7/70033; G03F 7/70925; G03F 7/70983; H01L 21/67253; G01P 3/68;
(Continued)

(56) References Cited

U.S. PATENT DOCUMENTS

| 6,424,733 B2* | 7/2002 | Langley | ............ | H01L 21/67167 |
| | | | | 348/125 |
| 6,757,645 B2* | 6/2004 | Chang | ........................ | G03F 1/26 |
| | | | | 703/13 |

(Continued)

*Primary Examiner* — David A Vanore
(74) *Attorney, Agent, or Firm* — Haynes and Boone, LLP

(57) ABSTRACT

A single-shot metrology for direct inspection of an entirety of the interior of an EUV vessel is provided. An EUV vessel including an inspection tool integrated with the EUV vessel is provided. During an inspection process, the inspection tool is moved into a primary focus region of the EUV vessel. While the inspection tool is disposed at the primary focus region and while providing a substantially uniform and constant light level to an interior of the EUV vessel by way of an illuminator, a panoramic image of an interior of the EUV vessel is captured by way of a single-shot of the inspection tool. Thereafter, a level of tin contamination on a plurality of components of the EUV vessel is quantified based on the panoramic image of the interior of the EUV vessel. The quantified level of contamination is compared to a KPI, and an OCAP may be implemented.

20 Claims, 9 Drawing Sheets

(51) Int. Cl.
  *G03F 7/20* (2006.01)
  *H01L 21/027* (2006.01)
  *G01N 21/956* (2006.01)

(52) U.S. Cl.
  CPC ........ *G03F 7/2037* (2013.01); *G03F 7/70033* (2013.01); *G03F 7/70166* (2013.01); *G03F 7/70175* (2013.01); *G03F 7/70916* (2013.01); *H01L 21/0275* (2013.01)

(58) Field of Classification Search
  CPC .......................... G02B 9/0095; G02B 27/0006; H04N 5/217; H04N 5/2171
  USPC ......... 250/504 R; 382/152, 145; 348/E5.028, 348/125, 207.99, 335; 356/337
  See application file for complete search history.

(56) References Cited

U.S. PATENT DOCUMENTS

| | | | |
|---|---|---|---|
| 6,940,554 B2 * | 9/2005 | Robins | G02B 27/0006 348/335 |
| 7,313,262 B2 * | 12/2007 | Lin | H01L 21/67253 118/719 |
| 7,525,115 B2 * | 4/2009 | Dobschal | B82Y 10/00 250/580 |
| 8,716,841 B1 | 5/2014 | Chang et al. | |
| 8,736,084 B2 | 5/2014 | Cheng et al. | |
| 8,764,995 B2 | 7/2014 | Chang et al. | |
| 8,796,666 B1 | 8/2014 | Huang et al. | |
| 8,828,625 B2 | 9/2014 | Lu et al. | |
| 8,837,810 B2 | 9/2014 | Chen et al. | |
| 8,841,047 B2 | 9/2014 | Yu et al. | |
| 8,877,409 B2 | 11/2014 | Hsu et al. | |
| 8,901,523 B1 | 12/2014 | Ershov et al. | |
| 9,093,530 B2 | 4/2015 | Huang et al. | |
| 9,134,633 B2 | 9/2015 | Lin et al. | |
| 9,184,054 B1 | 11/2015 | Huang et al. | |
| 9,230,867 B2 | 1/2016 | Cheng et al. | |
| 9,256,123 B2 | 2/2016 | Shih et al. | |
| 9,304,403 B2 | 4/2016 | Lin et al. | |
| 9,404,743 B2 | 8/2016 | Chiu et al. | |
| 9,529,268 B2 | 12/2016 | Chang et al. | |
| 9,548,303 B2 | 1/2017 | Lee et al. | |
| 9,778,022 B1 * | 10/2017 | Odle | G01B 11/002 |
| 9,857,690 B2 * | 1/2018 | Kim | G03F 7/70033 |
| 2012/0113513 A1 * | 5/2012 | Zhang | H01S 3/027 359/513 |
| 2017/0045832 A1 * | 2/2017 | Molkenboer | G03F 7/70925 |

* cited by examiner

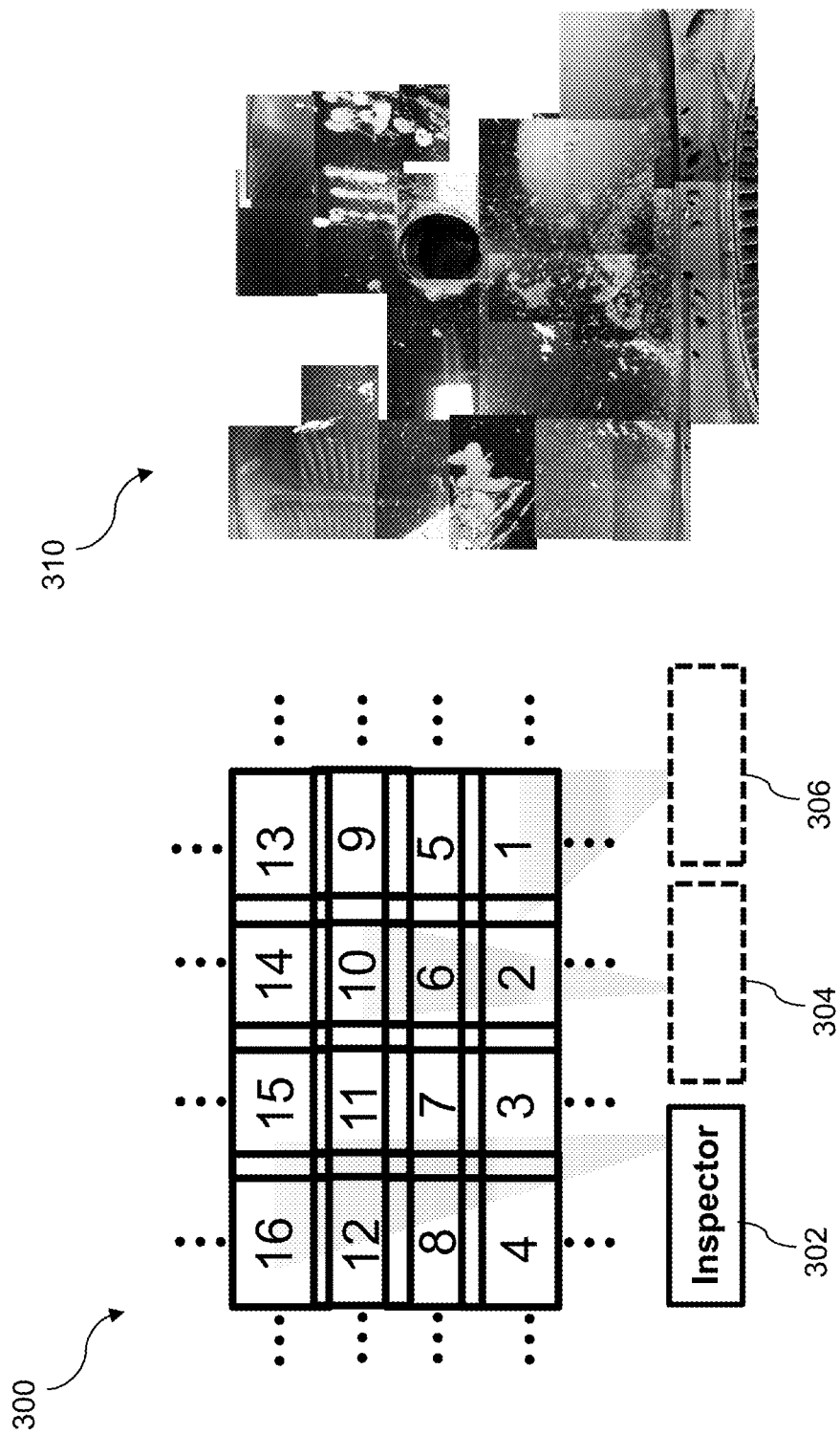

EUV VESSEL INSPECTION METHOD AND RELATED SYSTEM

CROSS-REFERENCE TO RELATED APPLICATION

This application claims the benefit of U.S. Provisional Application No. 62/539,273, filed Jul. 31, 2017, the entirety of which is incorporated by reference herein.

BACKGROUND

The electronics industry has experienced an ever increasing demand for smaller and faster electronic devices which are simultaneously able to support a greater number of increasingly complex and sophisticated functions. Accordingly, there is a continuing trend in the semiconductor industry to manufacture low-cost, high-performance, and low-power integrated circuits (ICs). Thus far these goals have been achieved in large part by scaling down semiconductor IC dimensions (e.g., minimum feature size) and thereby improving production efficiency and lowering associated costs. However, such scaling has also introduced increased complexity to the semiconductor manufacturing process. Thus, the realization of continued advances in semiconductor ICs and devices calls for similar advances in semiconductor manufacturing processes and technology.

As merely one example, semiconductor lithography processes may use lithographic templates (e.g., photomasks or reticles) to optically transfer patterns onto a substrate. Such a process may be accomplished, for example, by projection of a radiation source, through an intervening photomask or reticle, onto the substrate having a photosensitive material (e.g., photoresist) coating. The minimum feature size that may be patterned by way of such a lithography process is limited by the wavelength of the projected radiation source. In view of this, extreme ultraviolet (EUV) radiation sources and lithographic processes have been introduced. However, EUV systems, which utilize reflective rather than conventional refractive optics, are very sensitive to contamination issues. In one example, particle contamination introduced onto surfaces of an EUV vessel (e.g., within which EUV light is generated) can result in degradation of various components of the EUV vessel. As such, it is necessary to periodically inspect and perform preventive maintenance (PM) on the EUV vessel. At least some current EUV vessel inspection methods utilize a procedure that is merely qualitative and very time consuming. This can result in a non-optimal PM schedule, increased system downtime, and reduced system lifetime. Thus, existing EUV vessel inspection techniques have not proved entirely satisfactory in all respects.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 3A is an exemplary image capture sequence for capturing a plurality of images as part of a method to image an entirety of an interior of an EUV vessel;

FIG. 3B is a combination image which may be constructed from a plurality of images captured using the exemplary image capture sequence of FIG. 3A;

DETAILED DESCRIPTION

Figure 1:
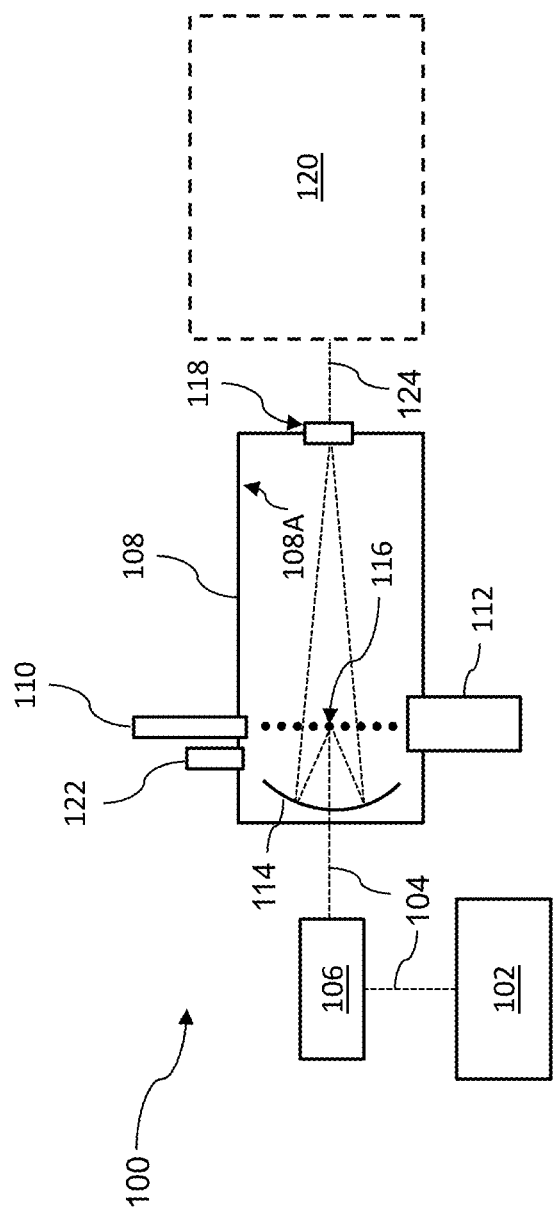
FIG. 1 is a schematic view of an EUV light source, including an exemplary EUV vessel, in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. Additionally, throughout the present disclosure, the terms "mask", "photomask", and "reticle" may be used interchangeably to refer to a lithographic template, such as an EUV mask.

As the minimum feature size of semiconductor integrated circuits (ICs) has continued to shrink, there has continued to be a great interest in photolithography systems and processes using radiation sources with shorter wavelengths. In view of this, extreme ultraviolet (EUV) radiation sources, processes, and systems (e.g., such as the lithography system 800 discussed with reference to FIG. 8) have been introduced. However, EUV systems, which utilize reflective rather than conventional refractive optics, are very sensitive to contamination issues. In one example, particle contamination introduced onto surfaces of an EUV vessel (e.g., within which EUV light is generated) can result in degradation of various components of the EUV vessel.

Referring to FIG. 1, illustrated therein is a schematic view of an EUV light source, including an exemplary EUV vessel. In some embodiments, an EUV light source 100 may include a laser produced plasma (LPP) EUV light source. Thus, as shown and in some embodiments, the EUV light source 100 may include a pulsed laser source 102 (e.g., such as a $CO_2$ laser) that generates and amplifies a high power laser beam 104. The laser beam 104 may then be directed, by a beam transport and focusing system 106, to an EUV vessel 108. In various embodiments, the EUV vessel 108 also includes a droplet generator 110 and a droplet catcher 112. In some cases, the droplet generator 110 provides droplets of tin or a tin compound into the EUV vessel 108. In addition, the EUV vessel 108 may include one or more optical elements such as a collector 114. In some embodiments, the collector 114 may include a normal incidence reflector, for example, implemented as a multilayer mirror (MLM). For example, the collector 114 may include a capping layer (e.g., silicon carbide, SiC) substrate coated with a Mo/Si multilayer. In some cases, one or more barrier layers may be formed at each interface of the MLM, for example, to block thermally-induced interlayer diffusion. In some examples, other substrate materials may be used for the collector 114 such as Al, Si, or other type of substrate materials. In some embodiments, the collector 114 includes an aperture through which the laser beam 104 may pass through and irradiate droplets generated by the droplet generator 110, thereby producing a plasma at an irradiation region 116. In some embodiments, the collector 114 may have a first focus at the irradiation region 116 and a second focus at an intermediate focus region 118. By way of example, the plasma generated at the irradiation region 116 produces EUV light 124 collected by the collector 114 and output from the EUV vessel 108 through the intermediate focus region 118. From there, the EUV light 124 may be transmitted to an EUV lithography system 120 for processing of a semiconductor substrate (e.g., such as discussed with reference to FIG. 8). In some embodiments, the EUV vessel 108 may also include a metrology apparatus 122, as discussed in more detail below.

Over time, the collector 114, as well as other interior surfaces 108A of the EUV vessel may become contaminated by material from the droplet generator 110 (e.g., tin). To maintain optimal performance and extend the lifetime of the EUV vessel 108, it is necessary to periodically inspect and perform preventive maintenance (PM) on the EUV vessel 108. Routine inspection of the EUV vessel 108 may be particularly important to prevent degradation of the collector 114, for example, and for management of various kinds of tin debris. In at least some current processes, deciding when to perform preventive maintenance (e.g., such as de-clogging the EUV vessel, EUV light collect swap, mirror and/or window cleaning), may be based merely on qualitative information that is both challenging to collect and process. For example, as part of the metrology apparatus 122, a camera adapted to an end of a rod or similar may be used to capture images of the interior of the EUV vessel 108.

Figure 2A:
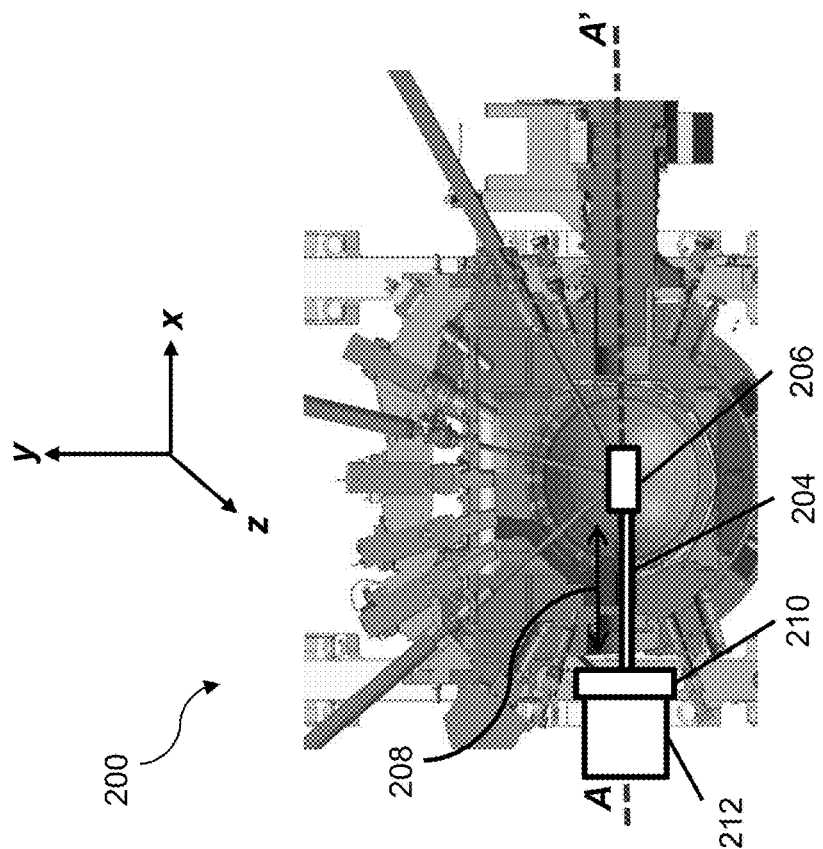
FIG. 2A is a top-down view of an EUV vessel, in accordance with some embodiments.
Figure 2B:
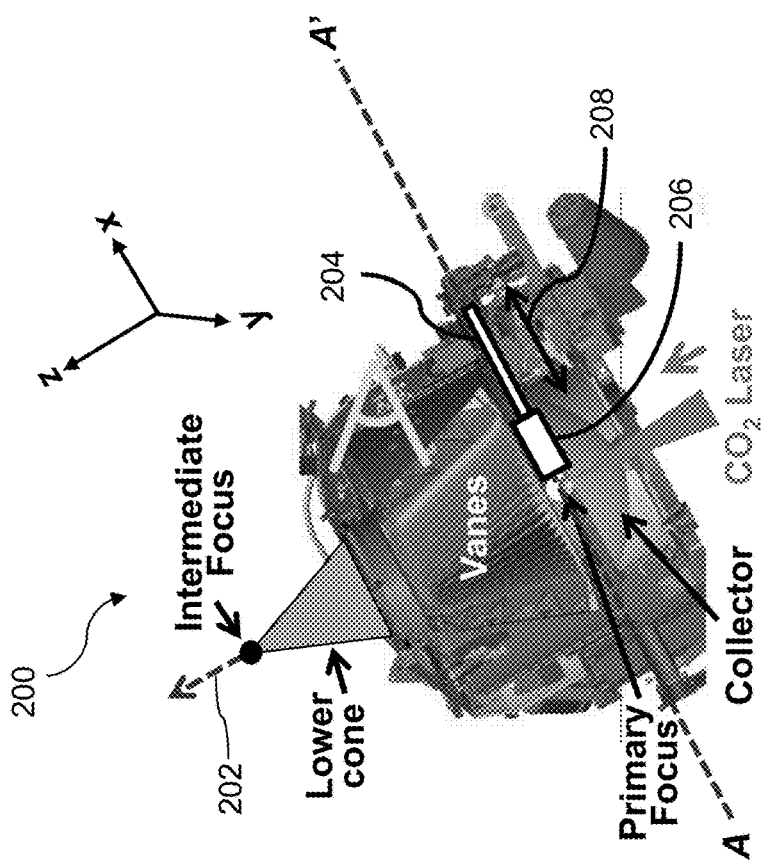
FIG. 2B is an end view of an EUV vessel, according to some embodiments.

Referring to FIGS. 2A and 2B, illustrated therein are schematic views of an EUV vessel 200 (e.g., similar to the EUV vessel 108), which provide further details. For example, FIG. 2A shows a top-down view of the EUV vessel 200 which illustrates a collector (e.g., such as the collector 114), a primary focus (e.g., such as the first focus described above), entry of a $CO_2$ laser (e.g., such as the laser beam 104) through the collector aperture, and EUV light 202 output from the EUV vessel 200 through the intermediate focus region. In some embodiments, the EUV vessel 200 may also include a plurality of vanes. By way of example, the plurality of vanes may be used to assist in the prevention of source material accumulation (e.g., tin accumulation) on at least some interior surfaces of the EUV vessel 200. Thus, in some cases, each of the plurality of vanes may be heated to a melting point of material provided by the droplet generator 110 (e.g., tin) such that the melted material may flow (e.g., along a vane fluid channel) into a collection sump. While the vanes may help to reduce at least some EUV vessel 200 contamination, periodic inspection and maintenance is nevertheless required.

FIGS. 2A and 2B also show a rod 204 having a camera 206 adapted thereto. In some embodiments, the rod 204 and camera 206 may be implemented as part of a borescope through a port of the EUV vessel 200. FIG. 2B, which provides an end-view of the EUV vessel 200, also illustrates a satellite chamber 212 (e.g., coupled to a side of the EUV vessel 200 and to the rod 204) and a gate valve 210, for example, through which the borescope passes. For purposes of this disclosure, and in some cases, the camera 206 may be equivalently referred to as an "inspector". In at least some current methods, and because the camera used has a limited field of view, a plurality of images are needed in order to adequately image an entirety of an interior of the EUV vessel 200. In other words, existing methods do not provide for capture of an entirety of an interior of the EUV vessel 200 using a single camera shot. Instead, by rotating and/or extending the rod 204 to which the camera 206 is attached (e.g., as indicated by arrow 208), an entirety of the interior of the EUV vessel 200 may be captured, in accordance with at least some existing methods. However, such methods require at least tens of images having different levels of backlight illumination. In addition, the field of view of each image of the plurality of images is different due to lack of precise mechanical manipulation (e.g., of the rod 204 and/or camera 206). After capture of the plurality of images, a combination image may be constructed by combining each image of the plurality of images (e.g., similar to a jigsaw puzzle). However, such a combination image provides, at best, a qualitative characterization of the tin contamination of EUV vessel 200. Thus, without data quantification (e.g., of the contamination), corresponding defensing and/or preventive measures cannot be adequately prepared. Stated another way, the plurality of images collected by such existing methods provide only an indirect inspection technique by attempting to quantify collector tin contamination by measuring an EUV reflection profile from scanner side (e.g., from direction of the EUV lithography system 120 of FIG. 1).

With reference to FIG. 3A, illustrated therein is an exemplary image capture sequence 300 (e.g., using the rod 204 and camera 206) for capturing at least a portion of the plurality of images that may be captured as part of the method to image an entirety of an interior of the EUV vessel 200. In some examples, the image capture sequence 300 may be used to capture a plurality of images of limited portions (e.g., due to the limited field of view of the camera 206) of the collector or the lower cone, for example, depending on an orientation and position of the rod 204 and the camera 206. As shown in the example of FIG. 3A, the image capture sequence 300 may include sixteen or more images, as numbered therein (e.g., for the reflection surface of the collector 114). In various cases, each of the plurality of images is captured with the inspector (e.g., the camera 206) at a different position, such as positions 302, 304, 306. Of course, many more positions and orientations may be needed to capture a completed set of images, in accordance with at least some existing methods. As discussed above, the captured plurality of images may be used to construct a combination image 310, as shown in FIG. 3B. In the present example, the combination image 310 may be an image of a collector. From the combination image 310, it is clear that such a combination image provides, at best, a qualitative characterization of contamination.

Generally, for collector tin contamination, at least 50 images (e.g., 50 shots) may be required to inspect an entirety of the interior surface of the EUV vessel, for example, due to the limited field of view of the camera/inspector and short distance inside the vessel. This can be a very time-consuming procedure. In addition, such existing methods require a post-data process to construct a combination image, which is also quite time-consuming. Moreover, as discussed above, the contamination (e.g., tin contamination) of the EUV vessel cannot be quantified at least because it can be quite difficult to maintain the illumination and the field of view the same for each shot (e.g., for each image capture). Without data quantification, key performance indicators (KPIs) cannot be defined, for example, for alarm conditions and/or for following an out-of-control action plan (OCAP). For EUV vessel tin contamination, the same difficulty is encountered by using a borescope with a limited field of view.

Embodiments of the present disclosure offer advantages over the existing art, though it is understood that other embodiments may offer different advantages, not all advantages are necessarily discussed herein, and no particular advantage is required for all embodiments. For example, embodiments of the present disclosure provide an inspection tool and related method that may be used to image an entirety of the EUV vessel using a single shot. As such, the present disclosure provides a single-shot method for direct inspection of an entirety of the interior of the EUV vessel, including providing for quantification of contamination (e.g., tin contamination). In some embodiments, the disclosed inspection tool and single-shot method may be used to image an entirety of an interior of the EUV vessel including a $CO_2$ mirror (e.g., a $CO_2$ laser mirror), an EUV collector, a droplet generation and tin catcher port, a lower cone, vanes (e.g., tin vanes) and a front-side scrubber, among other components. In various embodiments, the disclosed inspection tool includes a panoramic camera, an illuminator for providing a uniform and constant light level (e.g., to visualize tin debris), and a vacuum system for camera storage and manipulation. In some embodiments, the panoramic camera is vacuum compatible. In addition, and in some embodiments, the panoramic camera includes two fish-eye camera lenses (e.g., on opposing sides of each other) to provide a skydome view in a single shot, together with the uniform illuminator. In some embodiments, the disclosed vacuum system includes a gate valve and a satellite chamber for camera storage, and a mechanism for mechanical transport (e.g., a rod) of the camera from the satellite chamber to a primary focus region of the EUV vessel. In various embodiments, an image processing system may be used to transform the captured single-shot skydome view into a plane surface image, after which the EUV vessel contamination can be quantified, for example, by comparison of a current image to previous images (e.g., for any of a plurality of specified components of the EUV vessel). In some examples, the comparison may be made to an image that conforms to a defined KPI specification. In various examples, the contamination quantification may be performed by a local or remote image and/or data processing system. In addition, and because embodiments of the present disclosure provide for quantification of EUV vessel contamination, KPIs of tin contamination for the $CO_2$ mirror, the EUV collector, the droplet generation and tin catcher port, the lower cone, the vanes and the front-side scrubber can be determined. In some embodiments, KPIs of tin contamination may likewise be determined for other components of the EUV vessel. Further, and as a result of defining the KPIs, an inline monitor of EUV vessel tin contamination can be established and an alarm can be set, thereby providing a defensive system via an advanced data collection (ADC)/fault detection and classification (FDC) cloud-based data system. Thus, embodiments of the present disclosure provide a time-saving approach for EUV vessel inspection by providing for imaging of all EUV vessel components (e.g., such as the collector, the lower cone, the tin vanes, etc.) within an entirety of the interior of the EUV vessel with a single camera shot. Thus, embodiments disclosed herein provide for quantification of an amount of various tin contaminants, as well as collector degradation, within the EUV vessel, thereby enabling a corresponding defensive system and providing for more efficient troubleshooting. Further, the various embodiments disclosed herein provide for tin contamination to be routinely quantified and visualized, which facilitates action plan design (e.g., maintenance) to extend the lifetime of the EUV source vessel and the collector, among other system components. The disclosed inspection tool and single-shot method can also significantly reduce the time routinely spent for inspection and post-data processing by 92%, from about 120 minutes (currently) to less than about 10 minutes. Moreover, embodiments of the present disclosure can be used to increase the weekly tool availability by 1.1% and the productivity and working hours by nearly 2 hours. Further, various embodiments disclosed herein provide for improved monitoring and control of power degradation rate, which can directly impact wafer productivity. Those skilled in the art will recognize other benefits and advantages of the methods and inspection tool as described herein, and the embodiments described are not meant to be limiting beyond what is specifically recited in the claims that follow.

Figure 4A:
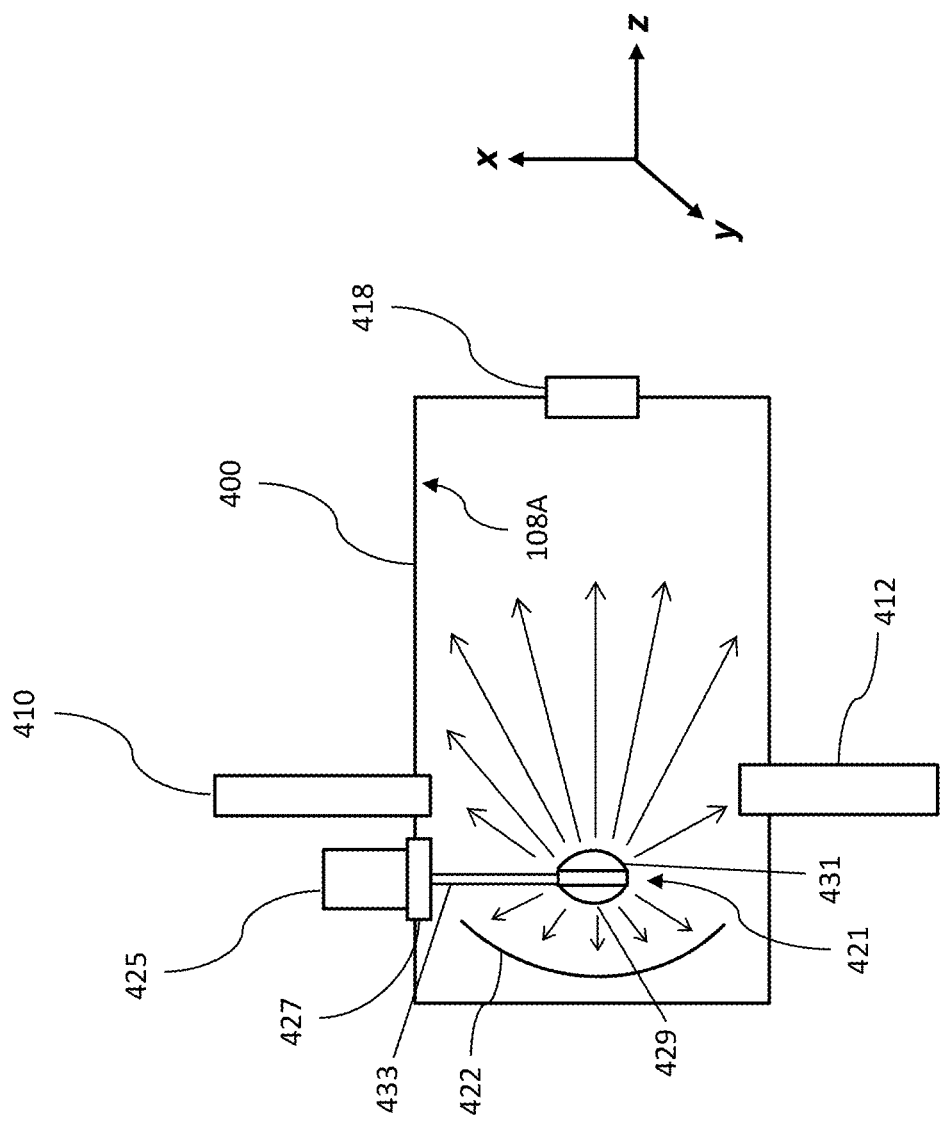
FIG. 4A is a schematic view of an EUV vessel, in accordance with some embodiments.

Referring now to FIG. 4A, illustrated therein is a schematic view of an EUV vessel 400, in accordance with some embodiments. One or more aspects of the EUV vessel 400 may be substantially similar to the EUV vessels 108, 200, described above. Thus, for the sake of clarity, some features may only be briefly described. As shown in FIG. 4A, the EUV vessel 400 may include a droplet generator 410 and a droplet catcher 412, as described above. In various embodiments, the EUV vessel 400 may also include one or more optical elements such as a collector 422. In some embodiments, the EUV vessel 400 includes a satellite chamber 425 and a gate valve 427. In some examples, a panoramic camera 421 including two opposing fish-eye camera lenses 429, 431 may be mounted to an end of a mechanical transport mechanism 433 (e.g., a retractable rod 433). In various embodiments, each of the fish-eye camera lenses 429, 431 may have an angle of view in a range from about 100 to 180 degrees. In addition, and in some cases, an illuminator having a uniform and constant light level may also be mounted at or near the end of the retractable rod 433 (e.g., adjacent to the panoramic camera). In some embodiments, the satellite chamber 425 is kept under vacuum condition and is used for camera storage and for protection from tin contamination (e.g., when the gate valve 427 is closed and the retractable rod 433 is retracted). Alternatively, during an inspection process, the gate valve 427 may be opened, and the retractable rod 433 is extended to move the panoramic camera from the satellite chamber 425 to a primary focus region of the EUV vessel 400. Thereafter, while positioned at the primary focus region of the EUV vessel 400 and with the illuminator providing the uniform and constant light level, a single-shot may be taken by way of the panoramic camera to capture an entirety of the interior of the EUV vessel 400. By way of example, the fish-eye lens 429 may be used to capture a first interior portion of the EUV vessel 400 in the direction of the collector 422, while the fish-eye lens 431 may be used to capture a second interior portion of the EUV vessel 400 in the direction of an intermediate focus region 418 (e.g., including the lower cone, vanes, droplet generation and tin catcher port, etc.). Thus, in combination, the dual fish-eye lenses 429, 431 may be used to capture an entirety of the interior of the EUV vessel 400 in a single camera shot. In some embodiments, a full 360 degree panoramic image may be constructed from the single-shot image captured by the dual fish-eye lenses 429, 431.

Figure 4C:
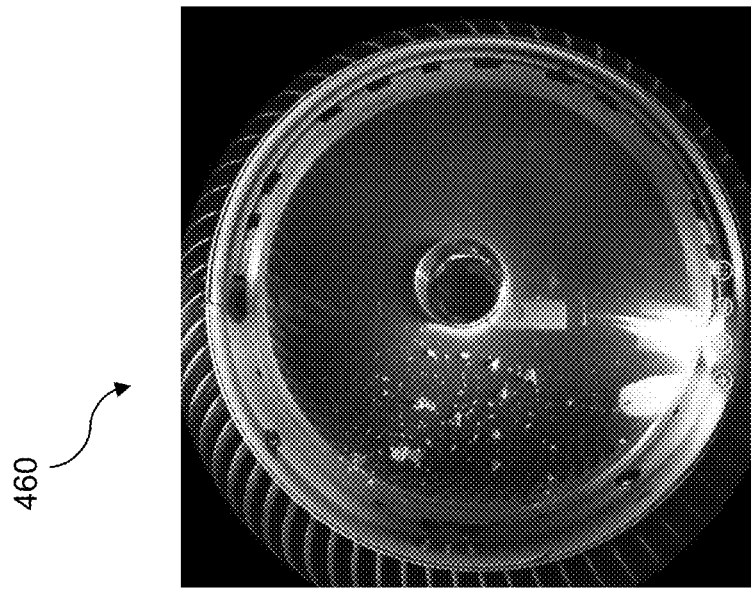
FIG. 4C is an example image captured using the exemplary image capture single-shot sequence of FIG. 4B.
Figure 4B:
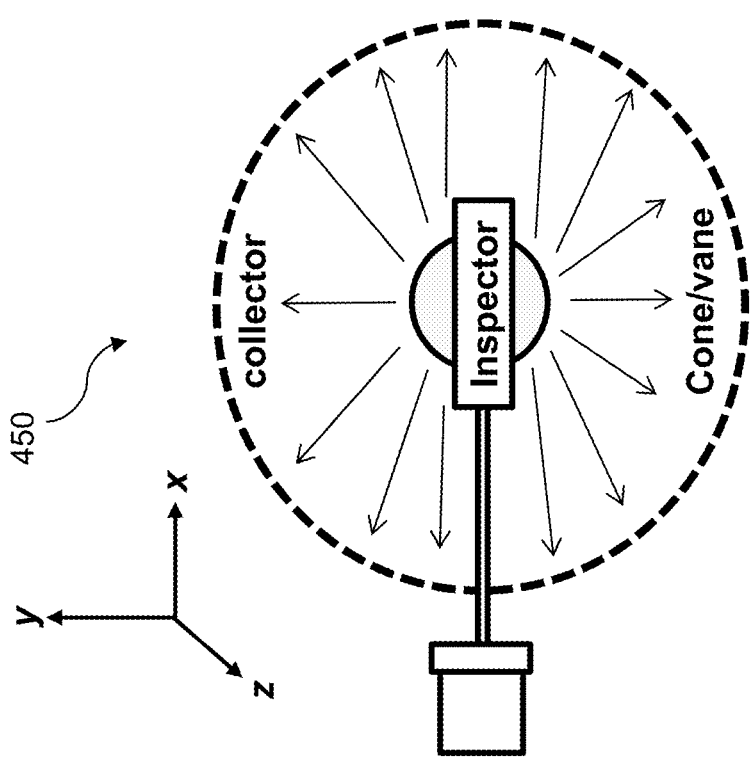
FIG. 4B is an exemplary image capture single-shot sequence for imaging an entirety of an interior of an EUV vessel, according to some embodiments.
Figure 5A:
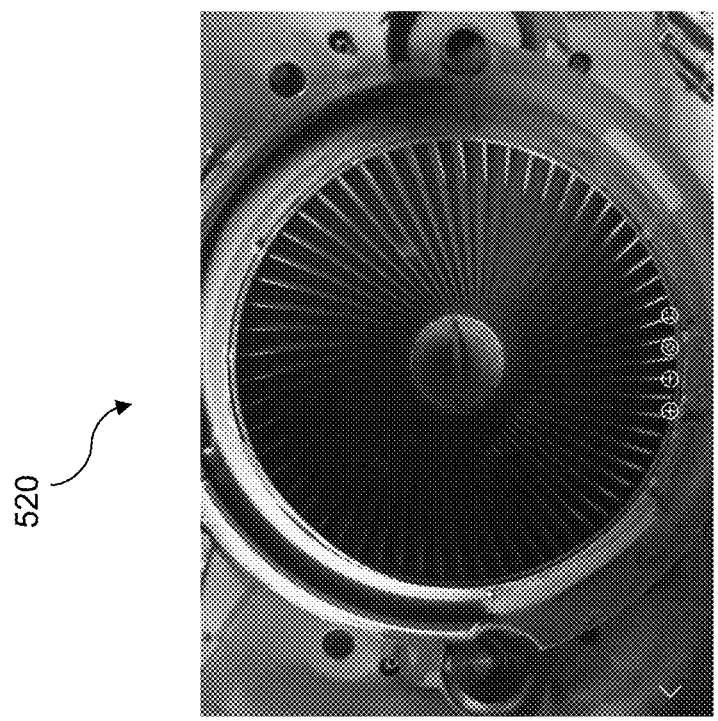
FIG. 5A shows another combination image which may be constructed from a plurality of images captured using the exemplary image capture sequence of FIG. 3A.
Figure 5B:
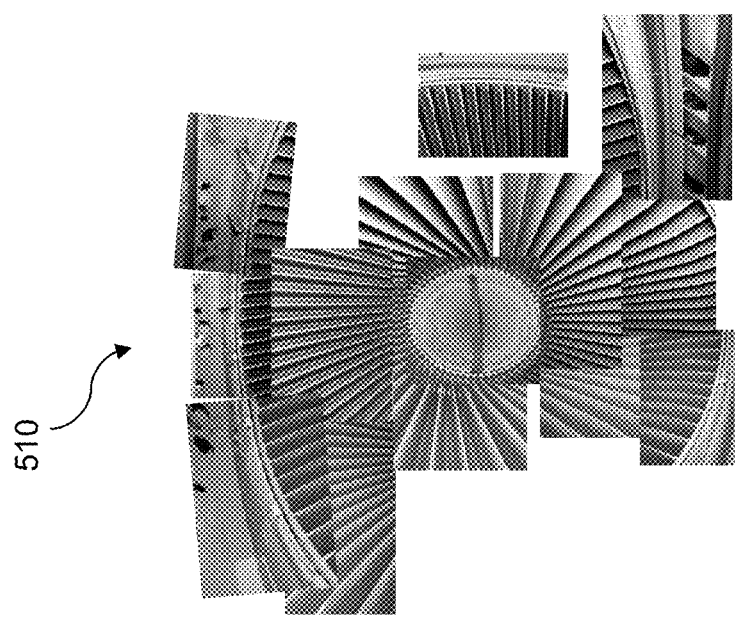
FIG. 5B shows another example of an image captured using the exemplary image capture single-shot sequence of FIG. 4B.

With reference to FIG. 4B, illustrated therein is an exemplary image capture single-shot sequence 450 (e.g., using the panoramic camera including the two fish-eye camera lenses 429, 431) for imaging an entirety of an interior of the EUV vessel 400 in a single camera shot. In contrast to the image capture sequence 300 described above, the image capture sequence 450 includes a single camera shot, where for example one of the two fish-eye lenses may be directed toward the collector while the other fish-eye lens is directed to the lower cone. Thus, rather than having to construct a combination image, such as the combination image 310 of FIG. 3B, embodiments of the present disclosure provide for a complete imaging of the interior of the EUV vessel 400 with a single shot. As one example, FIG. 4C shows an exemplary image 460 of a collector of the EUV vessel, taken using the panoramic camera and single-shot method disclosed herein. From the image 460, it is clear that a quantitative characterization of contamination can now be accurately provided. As a result, KPIs of tin contamination can be determined, an inline monitor of EUV vessel tin contamination can be established and an alarm can be set, thereby providing a defensive system via the ADC/FDC cloud-based data system. As an additional example, FIG. 5A shows a combination image 510 (e.g., of a lower cone portion) constructed from a plurality of images, in accordance with at least some existing methods, and FIG. 5B shows an image 520 of the same region shown in FIG. 5A, with the image 520 captured using the panoramic camera and single-shot method disclosed herein. This side-by-side comparison of images serves to further underscore not only the time-saving advantages provided (e.g., time reduced from about 120 minutes to less than 10 minutes), but also the ability to now effectively quantify tin contamination with the EUV vessel.

Figure 6:
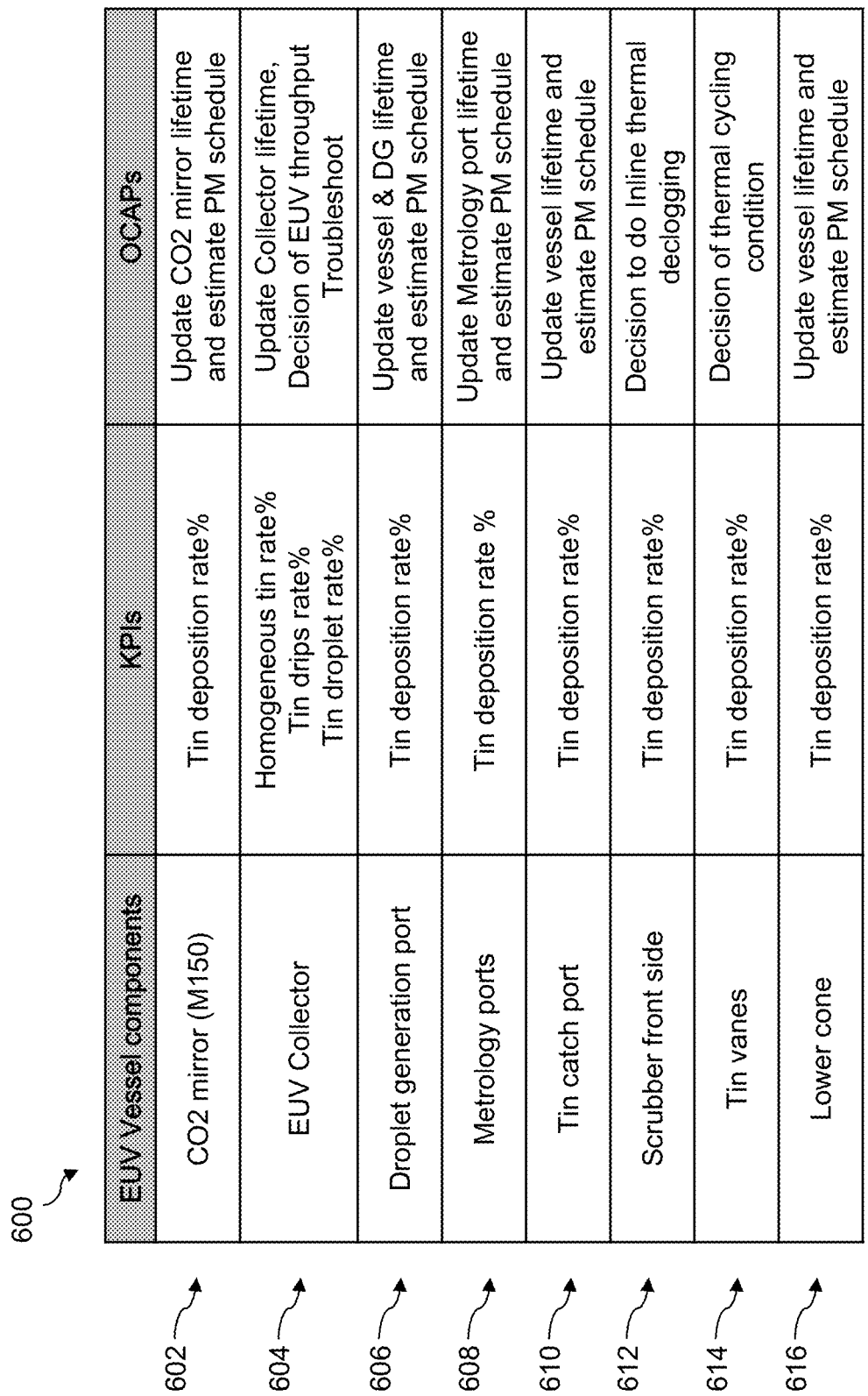
FIG. 6 shows a table that provides an exemplary list of EUV vessel components for which KPIs may be defined, and for which OCAPs may be established, in accordance with some embodiments.

As described above, embodiments of the present disclosure provide for a determination of key performance indicators (KPIs) for a variety of EUV vessel components. As a result of defining the KPIs, an inline monitor of EUV vessel tin contamination can be established and an alarm can be set, thereby providing a defensive system via an ADC/FDC cloud-based data system, for example, for alarm conditions and/or for following an OCPA. With reference to FIG. 6, illustrated therein is a table 600 that provides an exemplary list of EUV vessel components for which KPIs may be defined, and for which OCAPs may be established. For example, as shown in row 602 of table 600, a KPI for a $CO_2$ mirror may be defined as a tin deposition rate %. In this example, after capture and transformation of the single-shot image into a plane surface image, the $CO_2$ mirror contamination (e.g., and thus tin deposition rate %) can be quantified and compared to the defined KPI. In some embodiments, the quantification and KPI comparison may be performed by the ADC/FDC could-based system, which may include an image and/or data processing system. Thereafter, based on the results of the KPI comparison and in some embodiments, an OCAP may be implemented. In the present example of the $CO_2$ mirror, the OCAP may include updating the $CO_2$ mirror lifetime and estimated PM schedule. In various embodiments, similar procedures may be implemented for other defined KPIs. For example, row 604 of table 600 illustrates that KPIs for an EUV collector may be defined as a homogenous tin rate %, a tin drips rate %, and a tin droplet rate %. For the example of the EUV collector, the OCAP may include updating the collector lifetime, determining an EUV throughput, and deciding whether to troubleshoot the EUV collector. Row 606 of table 600 illustrates that a KPI for a droplet generation port may be defined as a tin deposition rate %, and the OCAP may include updating the EUV vessel and droplet generator lifetime, as well as the estimated PM schedule. Row 608 of table 600 illustrates that a KPI for one or more metrology ports may be defined as a tin deposition rate %, and the OCAP may include updating the metrology port lifetime and the estimated PM schedule. Row 610 of table 600 illustrates that a KPI for a tin catch port may be defined as a tin deposition rate %, and the OCAP may include updating the EUV vessel lifetime and the estimated PM schedule. Row 612 of table 600 illustrates that a KPI for a front-side scrubber may be defined as a tin deposition rate %, and the OCAP may include deciding whether to perform an inline thermal de-clogging procedure. Row 614 of table 600 illustrates that a KPI for the vanes (e.g., the tin vanes) may be defined as a tin deposition rate %, and the OCAP may include deciding whether to perform a thermal cycling process. Row 616 of table 600 illustrates that a KPI for the lower cone may be defined as a tin deposition rate %, and the OCAP may include updating the EUV vessel lifetime and the estimated PM schedule. While table 600 provided some examples of EUV vessel components for which KPIs may be defined and for which OCAPs may be established, these examples are not meant to be limiting in any way, and it will be understood that other EUV vessel components, other KPIs, and/or other OCAPs may equally be defined without departing from the scope of the present disclosure.

Figure 7:
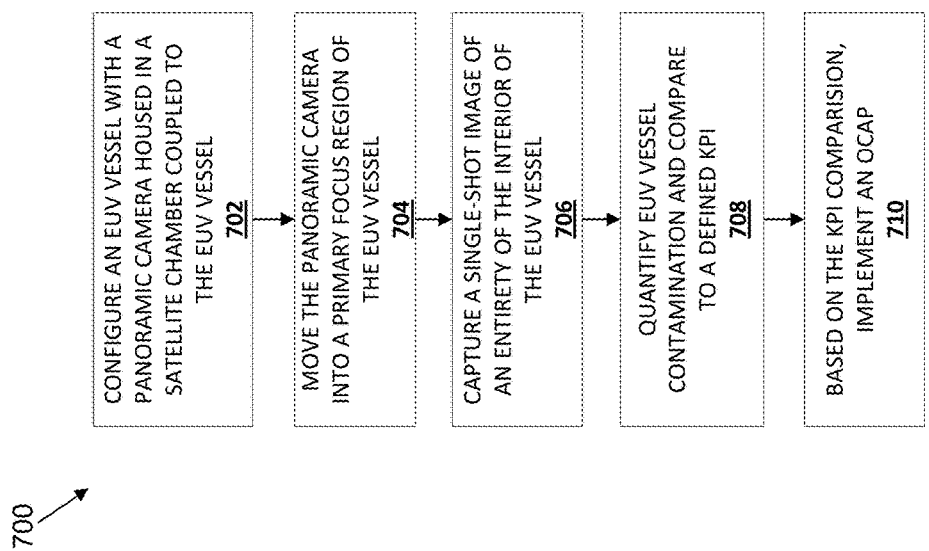
FIG. 7 is a flow chart of a method for imaging an entirety of an interior of an EUV vessel using a single camera shot, according to one or more aspects of the present disclosure.

Referring now to FIG. 7, illustrated therein are flow chart of a method 700 for imaging an entirety of an interior of an EUV vessel using a single camera shot, according to one or more aspects of the present disclosure. It is noted that the process steps of the method 700, including any descriptions given with reference to the figures, are merely exemplary and are not intended to be limiting beyond what is specifically recited in the claims that follow. Moreover, additional process steps may be implemented before, during, and after the method 700, and some process steps may be replaced or eliminated in accordance with various embodiments of the method 700.

The method 700 begins at block 702 where an EUV vessel is configured with a panoramic camera housed in a satellite chamber coupled to the EUV vessel. By way of example, and in some embodiments, the EUV vessel may be the EUV vessel 400, as shown in FIG. 4A. As such, in various embodiments, the EUV vessel may include the satellite chamber 425 coupled to an interior of the EUV vessel via the gate valve 427. In addition, the panoramic camera may include the two opposing fish-eye camera lenses 429, 431 which may be mounted to an end of the retractable rod 433. In some cases, an illuminator having a uniform and constant light level may also be mounted at or near the end of the retractable rod 433. In some cases, the EUV vessel may provide an EUV light source for a lithography system, such as described with reference to FIG. 8.

The method 700 then proceeds to block 704 where the panoramic camera is transversely moved into a primary focus region of the EUV vessel. For example, as part of an inspection process of the interior of the EUV vessel, the gate valve 427 may be opened, and the retractable rod 433 is extended to move the panoramic camera from the satellite chamber 425 to a primary focus region of the EUV vessel (e.g., as shown in FIG. 4A).

The method 700 then proceeds to block 706 where a single-shot image of an entirety of the interior of the EUV vessel is captured. For example, while the panoramic camera is positioned at the primary focus region of the EUV vessel and with the illuminator providing the uniform and constant light level, a single-shot may be taken by way of the panoramic camera to capture an entirety of the interior of the EUV vessel. In some cases, a first fish-eye lens of the panoramic camera may be used to capture a first interior portion of the EUV vessel (e.g., in a direction of the collector), while a second fish-eye lens of the panoramic camera may be used to capture a second interior portion of the EUV vessel (e.g., in a direction of an intermediate focus region). Thus, in combination, the first and second fish-eye lenses may be used to capture an entirety of the interior of the EUV vessel in a single camera shot.

The method 700 then proceeds to block 708 wherein EUV vessel contamination is quantified and compared to a defined KPI. In some embodiments, the EUV vessel contamination quantification and KPI comparison may be performed by the ADC/FDC could-based system, which may include an image and/or data processing system, as described above. At least some examples of EUV vessel components for which KPIs may be defined are provided with reference to table 600 of FIG. 6. Thereafter, the method 700 proceeds to block 710 where based on the KPI comparison, an OCAP may be implemented. In various embodiments, the OCAP may include updating a lifetime on an EUV vessel component, deciding whether to perform a specific maintenance task, estimating a PM schedule, or other appropriate actions. Generally, by defining the KPIs and comparing the quantified EUV vessel contamination to the defined KPIs, an inline monitor of EUV vessel tin contamination can be established and an alarm can be set, thereby providing a defensive system via an ADC/FDC cloud-based data system, for example, for alarm conditions and/or for following an OCPA.

Figure 8:
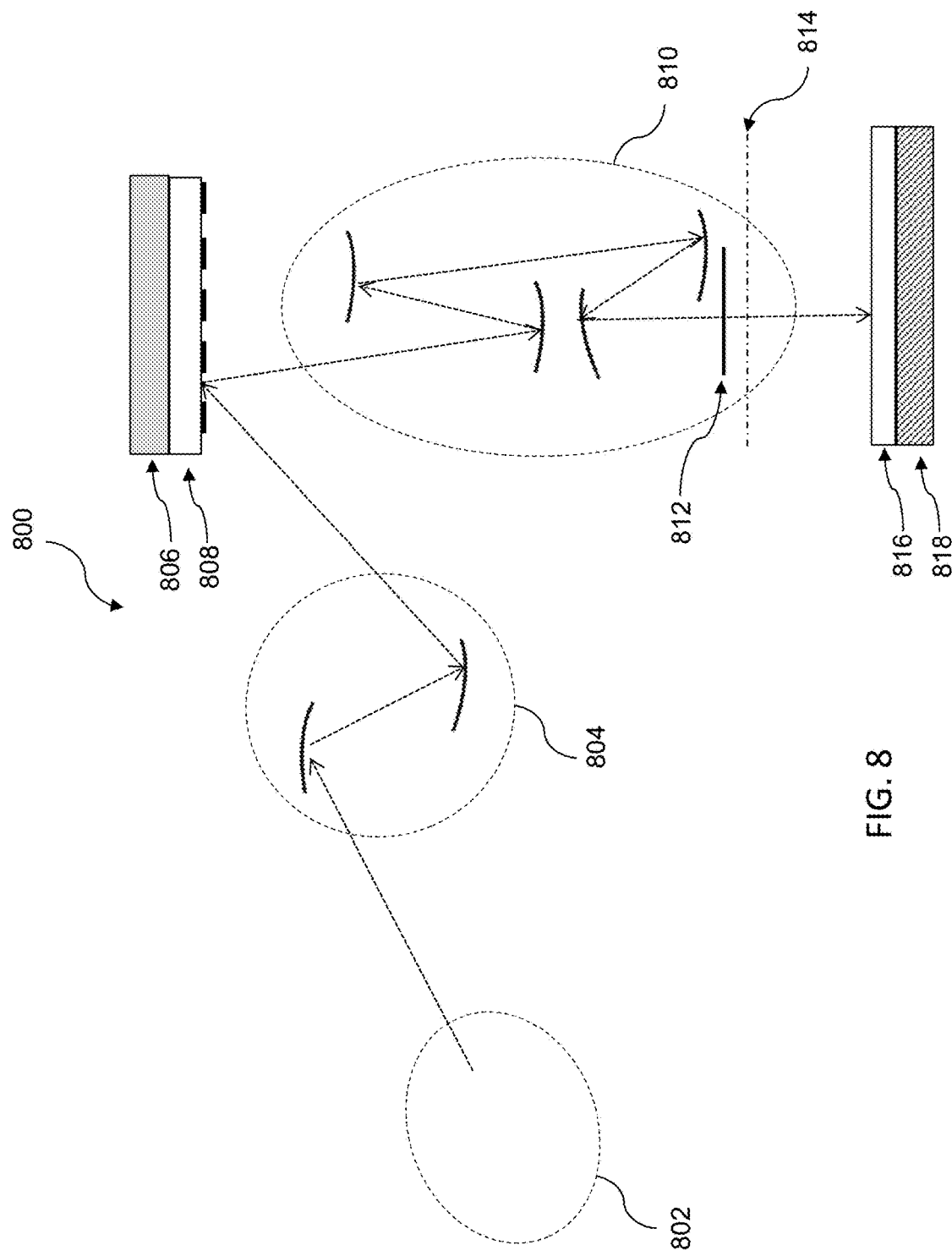
FIG. 8 is a schematic view of a lithography system, in accordance with some embodiments.

As previously noted, the EUV vessel described above may be used to provide an EUV light source for a lithography system. By way of illustration, and with reference to FIG. 8, provided therein is a schematic view of an exemplary lithography system 800, in accordance with some embodiments. The lithography system 800 may also be generically referred to as a scanner that is operable to perform lithographic processes including exposure with a respective radiation source and in a particular exposure mode. In at least some of the present embodiments, the lithography system 800 includes an extreme ultraviolet (EUV) lithography system designed to expose a resist layer by EUV light (e.g., provided via the EUV vessel). Inasmuch, in various embodiments, the resist layer includes a material sensitive to the EUV light (e.g., an EUV resist). The lithography system 800 of FIG. 8 includes a plurality of subsystems such as a radiation source 802 (e.g., such as the EUV light source 100 of FIG. 1), an illuminator 804, a mask stage 806 configured to receive a mask 808, projection optics 810, and a substrate stage 818 configured to receive a semiconductor substrate 816. A general description of the operation of the lithography system 800 may be given as follows: EUV light from the radiation source 802 is directed toward the illuminator 804 (which includes a set of reflective mirrors) and projected onto the reflective mask 808. A reflected mask image is directed toward the projection optics 810, which focuses the EUV light and projects the EUV light onto the semiconductor substrate 816 to expose an EUV resist layer deposited thereupon. Additionally, in various examples, each subsystem of the lithography system 800 may be housed in, and thus operate within, a high-vacuum environment, for example, to reduce atmospheric absorption of EUV light.

In the embodiments described herein, the radiation source 802 may be used to generate the EUV light. In some embodiments, the radiation source 802 includes a plasma source, such as for example, a discharge produced plasma (DPP) or a laser produced plasma (LPP). In some examples, the EUV light may include light having a wavelength ranging from about 1 nm to about 100 nm. In one particular example, the radiation source 802 generates EUV light with a wavelength centered at about 13.5 nm. Accordingly, the radiation source 802 may also be referred to as an EUV radiation source 802. In some embodiments, the radiation source 802 also includes a collector, which may be used to collect EUV light generated from the plasma source and to direct the EUV light toward imaging optics such as the illuminator 804.

As described above, light from the radiation source 802 is directed toward the illuminator 804. In some embodiments, the illuminator 804 may include reflective optics (e.g., for the EUV lithography system 800), such as a single mirror or a mirror system having multiple mirrors in order to direct light from the radiation source 802 onto the mask stage 806, and particularly to the mask 808 secured on the mask stage 806. In some examples, the illuminator 804 may include a zone plate, for example, to improve focus of the EUV light. In some embodiments, the illuminator 804 may be configured to shape the EUV light passing there through in accordance with a particular pupil shape, and including for example, a dipole shape, a quadrupole shape, an annular shape, a single beam shape, a multiple beam shape, and/or a combination thereof. In some embodiments, the illuminator 804 is operable to configure the mirrors (i.e., of the illuminator 804) to provide a desired illumination to the mask 808. In one example, the mirrors of the illuminator 804 are configurable to reflect EUV light to different illumination positions. In some embodiments, a stage prior to the illuminator 804 may additionally include other configurable mirrors that may be used to direct the EUV light to different illumination positions within the mirrors of the illuminator 804. In some embodiments, the illuminator 804 is configured to provide an on-axis illumination (ONI) to the mask 808. In some embodiments, the illuminator 804 is configured to provide an off-axis illumination (OAI) to the mask

808. It should be noted that the optics employed in the EUV lithography system 800, and in particular optics used for the illuminator 804 and the projection optics 810, may include mirrors having multilayer thin-film coatings known as Bragg reflectors. By way of example, such a multilayer thin-film coating may include alternating layers of Mo and Si, which provides for high reflectivity at EUV wavelengths (e.g., about 13.5 nm).

As discussed above, the lithography system 800 also includes the mask stage 806 configured to secure the mask 808. Since the lithography system 800 may be housed in, and thus operate within, a high-vacuum environment, the mask stage 806 may include an electrostatic chuck (e-chuck) to secure the mask 808. As with the optics of the EUV lithography system 800, the mask 808 is also reflective. As illustrated in the example of FIG. 8, light is reflected from the mask 808 and directed towards the projection optics 810, which collects the EUV light reflected from the mask 808. By way of example, the EUV light collected by the projection optics 810 (reflected from the mask 808) carries an image of the pattern defined by the mask 808. In various embodiments, the projection optics 810 provides for imaging the pattern of the mask 808 onto the semiconductor substrate 816 secured on the substrate stage 818 of the lithography system 800. In particular, in various embodiments, the projection optics 810 focuses the collected EUV light and projects the EUV light onto the semiconductor substrate 816 to expose an EUV resist layer deposited on the semiconductor substrate 816. As described above, the projection optics 810 may include reflective optics, as used in EUV lithography systems such as the lithography system 800. In some embodiments, the illuminator 804 and the projection optics 810 are collectively referred to as an optical module of the lithography system 800.

In some embodiments, the lithography system 800 also includes a pupil phase modulator 812 to modulate an optical phase of the EUV light directed from the mask 808, such that the light has a phase distribution along a projection pupil plane 814. In some embodiments, the pupil phase modulator 812 includes a mechanism to tune the reflective mirrors of the projection optics 810 for phase modulation. For example, in some embodiments, the mirrors of the projection optics 810 are configurable to reflect the EUV light through the pupil phase modulator 812, thereby modulating the phase of the light through the projection optics 810. In some embodiments, the pupil phase modulator 812 utilizes a pupil filter placed on the projection pupil plane 814. By way of example, the pupil filter may be employed to filter out specific spatial frequency components of the EUV light reflected from the mask 808. In some embodiments, the pupil filter may serve as a phase pupil filter that modulates the phase distribution of the light directed through the projection optics 810.

As discussed above, the lithography system 800 also includes the substrate stage 818 to secure the semiconductor substrate 816 to be patterned. In various embodiments, the semiconductor substrate 816 includes a semiconductor wafer, such as a silicon wafer, germanium wafer, silicon-germanium wafer, III-V wafer, or other type of wafer as described above or as known in the art. The semiconductor substrate 816 may be coated with a resist layer (e.g., an EUV resist layer) sensitive to EUV light. EUV resists may have stringent performance standards. For purposes of illustration, an EUV resist may be designed to provide at least around 22 nm resolution, at least around 2 nm line-width roughness (LWR), and with a sensitivity of at least around 15 mJ/cm$^2$. In the embodiments described herein, the various subsystems of the lithography system 800, including those described above, are integrated and are operable to perform lithography exposing processes including EUV lithography processes. To be sure, the lithography system 800 may further include other modules or subsystems which may be integrated with (or be coupled to) one or more of the subsystems or components described herein.

The various embodiments described herein offer several advantages over the existing art. It will be understood that not all advantages have been necessarily discussed herein, no particular advantage is required for all embodiments, and other embodiments may offer different advantages. For example, embodiments discussed herein provide an inspection tool and single-shot method for direct inspection of an entirety of the interior of the EUV vessel, including providing for quantification of contamination (e.g., tin contamination). In various embodiments, the disclosed inspection tool includes a panoramic camera, an illuminator that provides a uniform and constant light level, and a vacuum system for camera storage and manipulation. In some embodiments, the panoramic camera includes two fish-eye camera lenses (e.g., on opposing sides of each other) to provide a skydome view in a single shot, together with the uniform illuminator. In various embodiments, an image processing system may be used to transform the captured single-shot skydome view into a plane surface image, after which the EUV vessel contamination can be quantified, for example, by comparison of a current image to previous images (e.g., for any of a plurality of specified components of the EUV vessel). In some examples, the comparison may be made to an image that conforms to a defined KPI specification. Based on the results of the KPI comparison and in some embodiments, an OCAP may be implemented. Generally, embodiments of the present disclosure provide for an inline monitor of EUV vessel tin contamination and establishment of an alarm system, thereby providing a proactive defense to contamination of the EUV vessel. Thus, embodiments of the present disclosure serve to overcome various shortcomings of at least some existing EUV vessel inspection techniques.

Thus, one of the embodiments of the present disclosure described a method that includes providing a panoramic camera adapted for use within an extreme ultraviolet (EUV) vessel. In some embodiments, an image of an interior of the EUV vessel is captured, for example, by way of a single shot of the panoramic camera. In various examples, and based on the image of the interior of the EUV vessel, a level of contamination within the EUV vessel may then be quantified.

In another of the embodiments, discussed is a method where an EUV vessel including an inspection tool integrated with the EUV vessel is provided. In some cases, and during an inspection process, the inspection tool may be moved into a primary focus region of the EUV vessel. In some embodiments, while the inspection tool is disposed at the primary focus region and while providing a substantially uniform and constant light level to an interior of the EUV vessel by way of an illuminator, a panoramic image of an interior of the EUV vessel may be captured. Thereafter, in some embodiments, a level of tin contamination on a plurality of components of the EUV vessel may be quantified based on the panoramic image of the interior of the EUV vessel.

In yet another of the embodiments, discussed is an inspection system including an extreme ultraviolet (EUV) vessel configured for use as part of an EUV light source. In various embodiments, the inspection system also includes a satellite chamber coupled to a side of the EUV vessel, where a gate valve is disposed between the satellite chamber and the EUV vessel. In some embodiments, an inspection tool including a panoramic camera may be coupled to a first end of a mechanical transport mechanism, and a second end of the mechanical transport mechanism may be coupled to a portion of the satellite chamber. In some embodiments, the inspection system further includes an illuminator adjacently coupled to the panoramic camera. In various examples, the panoramic camera is configured, while disposed at a primary focus region of the EUV vessel, to capture an image of a plurality of components of the EUV vessel using a single shot of the panoramic camera. Moreover, and in some embodiments, the inspection system is configured to quantify, based on the captured image, a level of tin contamination on the plurality of components of the EUV vessel.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method, comprising:
providing a panoramic camera adapted for use within an extreme ultraviolet (EUV) vessel, wherein the panoramic camera includes two opposing fish-eye camera lenses;
capturing, by way of a single shot of the panoramic camera, an image of an interior of the EUV vessel; and
based on the image of the interior of the EUV vessel, quantifying a level of contamination within the EUV vessel.

2. The method of claim 1, wherein the captured image includes an image of an entirety of the interior of the EUV vessel.

3. The method of claim 1, further comprising:
while capturing the image, providing, by an illuminator disposed adjacent to the panoramic camera, a substantially uniform and constant light level to the interior of the EUV vessel.

4. The method of claim 1, further comprising:
capturing, by a first lens of the two opposing fish-eye camera lenses, a first image of the interior of the EUV vessel that includes a collector region; and
capturing, by a second lens of the two opposing fish-eye camera lenses, a second image of the interior of the EUV vessel that includes a lower cone region.

5. The method of claim 1, wherein the captured image includes a skydome view image, and wherein prior to quantifying the level of contamination, transforming the skydome view image, by an image processing system, into a plane surface image.

6. The method of claim 1, further comprising:
defining a key performance indicator (KPI) for at least one component of the EUV vessel; and
comparing the quantified level of contamination within the EUV vessel to the KPI.

7. The method of claim 6, wherein the defined KPI includes a tin deposition rate.

8. The method of claim 6, further comprising:
based on the comparing the quantified level of contamination within the EUV vessel to the KPI, implementing an out-of-control action plan (OCAP).

9. The method of claim 8, wherein the OCAP includes one or more of updating a lifetime of the at least one component of the EUV vessel, performing a maintenance task, and updating an estimated preventive maintenance (PM) schedule.

10. A method, comprising:
providing an extreme ultraviolet (EUV) vessel including an inspection tool integrated with the EUV vessel;
prior to and after an inspection process, housing the inspection tool in a satellite chamber coupled to the EUV vessel;
during the inspection process, moving the inspection tool into a primary focus region of the EUV vessel;
while the inspection tool is disposed at the primary focus region and while providing a substantially uniform and constant light level to an interior of the EUV vessel by way of an illuminator, capturing a panoramic image of an interior of the EUV vessel; and
based on the panoramic image of the interior of the EUV vessel, quantifying a level of tin contamination on a plurality of components of the EUV vessel.

11. The method of claim 10, wherein the plurality of components of the EUV vessel include a $CO_2$ mirror, an EUV collector, a droplet generation port, a tin catcher port, a metrology port, a lower cone, tin vanes, and a front-side scrubber.

12. The method of claim 10, wherein the inspection process is completed in less than about 10 minutes.

13. The method of claim 10, wherein the quantifying the level of tin contamination is performed by comparing the panoramic image to at least one previously captured image.

14. The method of claim 10, wherein the inspection tool includes two opposing fish-eye camera lenses.

15. An inspection system, comprising:
an extreme ultraviolet (EUV) vessel configured for use as part of an EUV light source;
a satellite chamber coupled to a side of the EUV vessel, wherein a gate valve is disposed between the satellite chamber and the EUV vessel;
an inspection tool including a panoramic camera coupled to a first end of a retractable rod, wherein a second end of the retractable rod is coupled to a portion of the satellite chamber; and
an illuminator adjacently coupled to the panoramic camera;
wherein the panoramic camera is configured, while disposed at a primary focus region of the EUV vessel, to capture a skydome view image of a plurality of components of the EUV vessel using a single shot of the panoramic camera; and
wherein an image processing system is configured to transform the skydome view image into a plane surface image, and wherein the image processing system is configured to quantify, based on the plane surface image, a level of tin contamination on the plurality of components of the EUV vessel.

16. The inspection system of claim 15, wherein the panoramic camera includes two opposing fish-eye camera lenses.

17. The inspection system of claim 15, wherein the gate valve is open and the retractable rod is extended while the panoramic camera is disposed at the primary focus region, and wherein the gate valve is closed and the retractable rod is retracted during storage of the panoramic camera which is protected from tin contamination within the satellite chamber.

18. The inspection system of claim 15, wherein the plurality of components of the EUV vessel include a $CO_2$ mirror, an EUV collector, a droplet generation port, a tin catcher port, a metrology port, a lower cone, tin vanes, and a front-side scrubber.

19. The method of claim 10, further comprising:
defining a key performance indicator (KPI) for at least one component of the EUV vessel, wherein the defined KPI includes a tin deposition rate;
comparing the quantified level of contamination within the EUV vessel to the defined KPI; and
based on the comparing, performing at least one of updating a lifetime of the at least one component of the EUV vessel, performing a maintenance task, and updating an estimated preventive maintenance (PM) schedule.

20. The inspection system of claim 16,
wherein a first lens of the two opposing fish-eye camera lenses is configured to capture a first portion of the skydome view image that includes a collector region; and
wherein a second lens of the two opposing fish-eye camera lenses is configured to capture a second portion of the skydome view image that includes a lower cone region.

* * * * *